United States Patent [19]

Deaton

[11] Patent Number: 5,049,484
[45] Date of Patent: Sep. 17, 1991

[54] PHOTOGRAPHIC SILVER HALIDE MATERIAL AND PROCESS

[75] Inventor: Joseph C. Deaton, Rochester, N.Y.

[73] Assignee: Eastman Kodak Company, Rochester, N.Y.

[21] Appl. No.: 614,537

[22] Filed: Nov. 16, 1990

[51] Int. Cl.$^5$ .............................................. G03C 1/09
[52] U.S. Cl. ..................................... 430/605; 430/612
[58] Field of Search ................................ 430/605, 612

[56] References Cited

U.S. PATENT DOCUMENTS

| 2,642,361 | 6/1953 | Damschroder et al. | 430/605 |
| 4,772,545 | 9/1988 | Nishiyama et al. | 430/564 |
| 4,810,626 | 3/1989 | Burgmaier et al. | 430/569 |

OTHER PUBLICATIONS

Research Disclosure, Item No. 308119, Dec. 1989, Section III & References mentioned therein.
Journal of Chem. Society Chem. Comm., 711 (1978), by Malik, Sadler, Neidle and Taylor.

Primary Examiner—Charles L. Bowers, Jr.
Assistant Examiner—Janet C. Baxter
Attorney, Agent, or Firm—Richard E. Knapp

[57] ABSTRACT

Improved chemical sensitization is provided by a photographic silver halide emulsion chemically sensitized with water-soluble gold(I) compound represented by the formula:

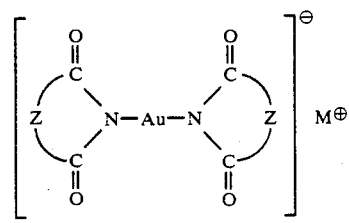

wherein Z represents the substituted or unsubstituted nitrogen and carbon atoms necessary to complete a 5- or 6-member imide nucleus; and M is a cation. Such a chemically sensitized photographic silver halide emulsion is useful in a photographic silver halide element and process.

10 Claims, No Drawings

PHOTOGRAPHIC SILVER HALIDE MATERIAL AND PROCESS

This invention relates to chemically sensitized silver halide photographic emulsions and photographic silver halide elements comprising such emulsions which have improved photosensitivity.

Chemical sensitization of silver halide photographic emulsions is known in the photographic art. This has been described in the photographic art, such as in *Research Disclosure*, Item 308119, December, 1989, paragraph III, and the references mentioned in this publication. Typically, silver halide photographic emulsions are chemically sensitized with sulfur, selenium, gold, platinum, palladium, iridium, osmium, rhenium, or phosphorous sensitizers or combinations of such chemical sensitizers or with reducing agents.

Gold compounds have been useful chemical sensitizers for such silver halide photographic emulsions. Such gold compounds can be in the (I) or (III) oxidation state. Gold(I) compounds provide an advantage over gold(III) compounds because the gold(I) compounds do not undergo detrimental side reactions which oxidize gelatin or other components of a silver halide photographic emulsion. Among gold(I) compounds which have been used as chemical sensitizers, aurous dithiosulfate has been commonly used. This gold(I) compound contains two thiosulfate ions bonded to the gold moiety. However, these thiosulfate ions present a problem in some cases because they undergo sulfur sensitization reactions in addition to the desired reaction. Aurous dithiosulfate is accordingly not useful in, for example, chemically sensitizing silver halide emulsions in which sulfur in an amount of less than 2:1 molar concentration with gold is desired in the sensitization. Aurous dithiosulfate is also not useful in other silver halide photographic emulsions in which sulfur or selenium sensitizers other than thiosulfates are desired, such as with sensitizers described in U.S. Pat. No. 4,810,626.

Other gold(I) compounds are known which do not contain thiosulfate ligands or other ligands possessing labile sulfur. However, the ligands in such gold(I) compounds have not been useful for chemical sensitization of silver halide emulsions because they are too strong as silver complexing agents. Thus, these gold(I) compounds, such as $KAu(SCN)_2$, provide unwanted continued complexing of silver when the ligands are dissociated from the gold(I). No answer to this problem has been available in the photographic art regarding gold chemical sensitization of silver halide photographic emulsions.

It has been desirable to provide a silver halide photographic emulsion which is chemically sensitized with a gold(I) compound, alone or in combination with other chemical sensitizers, which enables increased photosensitivity without undesired side reactions, such as undesired continued silver complexing activity.

It has been found that such advantages are provided by a photographic silver halide emulsion chemically sensitized with a water-soluble gold(I) compound represented by the formula:

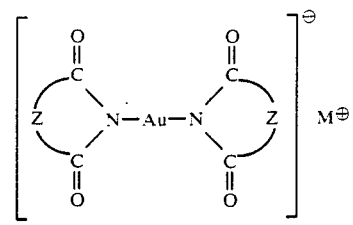

wherein Z represents the substituted or unsubstituted nitrogen and carbon atoms necessary to complete a 5- or 6 member imide nucleus; and M is a cation. The protonated form of the imide nucleus preferably has a pKa in the range of 7 to 12, and more preferably 8 to 11.

Z is preferably

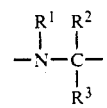

wherein $R^1$, $R^2$ and $R^3$ individually are hydrogen or a hydrocarbon group, preferably a substituted or unsubstituted hydrocarbon group containing 1 to 15 carbon atoms, such as an alkyl group, for example, methyl, ethyl, propyl, n-butyl and t-butyl, and octyl groups, or phenyl groups. $R^3$ is preferably hydrogen.

Typical examples of Z are:

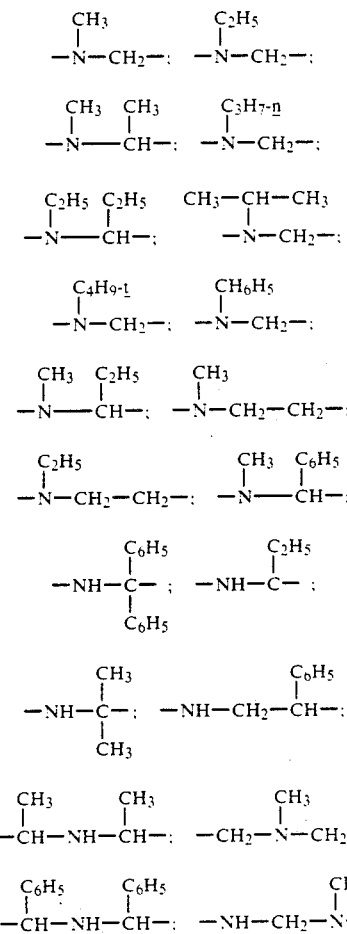

-continued $$-NH-\overset{O}{\underset{\|}{C}}-NH-; \quad -\overset{-CH_2C_6H_5}{\underset{|}{N}}-CH_2-;$$

M in the above formula can be any cation. M is preferably sodium, tetraethyl ammonium or potassium.

The gold(I) chemical sensitizers as described can be used in ways and for purposes that gold chemical sensitizers have been used in the photographic art. The method of chemical sensitization and the concentrations of chemical sensitizer as described can be any of the methods and concentrations known to be useful in the photographic art for chemical sensitization. The optimum concentration and method will depend upon the particular silver halide emulsion which is chemically sensitized, the desired degree of photosensitivity and other addenda used in the photographic silver halide emulsion. Typically, the concentration of the described chemical sensitizer used for chemical sensitization is within the range of $10^{-6}$ to $10^{-4}$ mole per silver mole.

Preferred chemical sensitizers as described are:

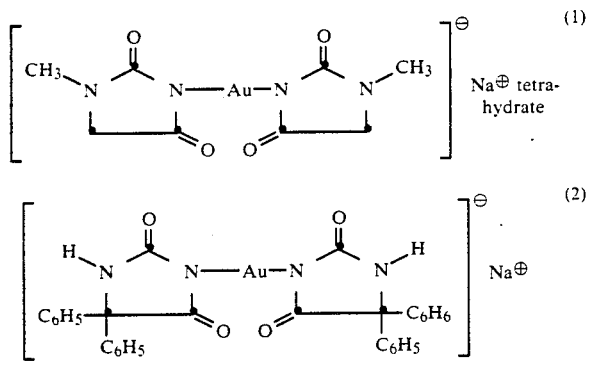

In the described gold(I) chemical sensitizers, the gold is bonded to the nitrogen atom of the anions of acidic nitrogen compounds. The nitrogen compounds preferably have pKa values within the range of 7 to 12. The pKa is determined by methods and means known in the photographic art.

When the anionic ligands in the gold(I) compounds as described are released from the gold in the silver halide emulsion, the ligands become protonated under the typical pH conditions of the photographic emulsions, such as a pH within the range of 4 to 8. This enables the ability of the ligands to complex metal ions, particularly silver ions, to be ended or switched off.

The synthesis of the described gold(I) compounds can be carried out by methods and means known in the inorganic chemistry art. The method described in, for example, *Journal of Chemical Society Chem. Comm.*, 711 (1978), by N. A. Malik, P. J. Sadler, S. Neidle and G. L. Taylor can be used for synthesis of the compounds. An example of a method of synthesis is as follows:

SYNTHESIS EXAMPLE A

An amount of 1.17 g 1-methylhydantoin is mixed with 1 ml water. Sodium hydroxide solution (approximately 5 molar concentration) is added dropwise to the slurry until the solid 1-methylhydantoin dissolves completely and the pH reaches a value between 10 and 11. An amount of 1.02 g NaAuCl$_4$.2H$_2$O is dissolved in 1 ml water and added dropwise to the basic solution of 1-methylhydantoin at room temperature. As the reaction proceeds, small amounts of the 5M NaOH solution are added to keep the pH between 10 and 11. A white precipitate begins to form, and the reaction mixture is stirred for an additional 20 min after the addition of the NaAuCl$_4$ is complete. After allowing the reaction mixture to stand in the freezer for an additional 20 min, the product is filtered. The product may be recrystallized by dissolving in the minimum amount of refluxing methanol (about 10 ml) and filtering while hot into a flask containing 0.5 ml water. The product, bis(1-methylhydantoinato) gold(I) sodium salt tetrahydrate, crystallizes as colorless needles upon standing in the freezer overnight.

This invention also provides a process for sensitizing a silver halide emulsion formed according to processes generally well-known in the art. A double jet-type process is preferred. The silver halide grains can comprise mixed or single halide components and especially include chloride, bromide, iodide, iodochloride, iodobromide or chlorobromide grains.

The double-jet process comprises adding an aqueous silver nitrate solution and an aqueous solution of one or more halides, for example, an alkali metal halide such as potassium bromide, potassium chloride, potassium iodide or mixtures thereof, simultaneously to a stirred solution of a silver halide protective colloid through two separate jets.

In the present invention, the described sensitizing gold(I) compounds may be added to a silver halide emulsion at various stages during its preparation. For example, the compounds may be added at levels from about $10^{-7}$ to about $10^{-3}$ mol thereof per mol of silver halide. A preferred concentration of gold compound to achieve sensitization of silver halide is from about $10^{-6}$ to about $10^{-4}$ mol thereof per mol of silver halide.

The gold sensitizing compounds may be added singly or in combination with other sensitizing agents. They may also be added to a silver halide emulsion along with silver ion ligands and silver halide growth modifiers or stabilizers and antifogging agents, or with spectral or chemical sensitizing agents such as sulfur or selenium compounds or with dopants such as iridium complexes, during formation of silver halide grains, during the physical or chemical ripening stage, or in a separate step before coating.

Conditions for sensitizing silver halide grains such as pH, pAg, temperature, etc., are not particularly limited when employed using compounds described herein. The pH is generally about 1 to 9, preferably about 3 to 6, and pAg is generally about 5 to about 12, preferably from about 7 to about 10. Silver halide grains may be sensitized at temperatures between about 30° to about 90° C., with about 40° to about 70° C. being preferred.

Gelatin is preferred as the binder or protective colloid for the photographic emulsion of the present invention. However, other hydrophilic colloids are also suitable. For example, proteins such as gelatin derivatives, graft polymers of gelatin and other polymers, albumin, casein, cellulose derivatives such as hydroxyethyl cellulose, carboxymethyl cellulose and cellulose sulfate, sugar derivatives such as sodium alginate, starch derivatives and various synthetic peptizers such as hydrophilic homopolymers or copolymers such as polyvinyl alcohol, poly-N-vinylpyrrolidone, polyacrylic acid, polymethacrylic acid, polyacrylamide, polyvinylimidazole and polyvinyl pyrazole can be used.

Acid-processed gelatin can be used, as well as lime-processed gelatin. Further, gelatin hydrolyzates and enzyme-hydrolyzed products of gelatin are also usable.

Surface-active agents may be incorporated in a photographic emulsion layer or in another hydrophilic colloid layer as a coating aid to prevent build-up of static charge, to improve lubrication properties, to improve emulsion dispersion, to prevent adhesion and to improve such photographic characteristics as acceleration of development, increase in contrast, or sensitization.

A photosensitive material of the present invention may contain antifogging agents or emulsion-stabilizing agents such as, for example, azaindenes, thionamides, azoles and the like.

The photosensitive emulsion as described may be spectrally sensitized with dyes. Dyes which can be used include cyanine dyes, merocyanine dyes, composite cyanine dyes, composite merocyanine dyes and hemioxanol dyes. Particularly useful dyes are those belonging to the merocyanine class. These dyes contain as a basic heterocyclic-ring nucleus any nucleus ordinarily used in cyanine dyes.

The photographic silver halide which is chemically sensitized as described can be any photographic silver halide known in the photographic art. Preferred silver halides are silver bromide, silver chloride, silver bromoiodide, silver bromochloride, silver chloroiodide and silver chloroiodide and combinations thereof. The silver halide emulsions can be negative-working or direct-positive emulsions. The silver halide can be any grain size and grain shape shown in the photographic art. The emulsions can include coarse-, medium- or fine-grain silver halide grains. Particularly useful grain shapes include cubic, octahedral, cubo-octahedral and tabular grains. Tabular-grain photographic silver halides are particularly useful, such as described in *Research Disclosure*, January, 1983, Item 22534, and U.S. Pat. No. 4,434,226. Also specifically contemplated are those silver bromoiodide grains with a higher molar proportion of iodide in the core of the grain than in the periphery of the grain as known in the photographic art.

Photographic elements in which the described silver halide photographic emulsions are useful can be simple elements comprising a support and a single silver halide emulsion layer or they can be multilayer, multicolor photographic elements. A typical multilayer, multicolor photographic element as described can comprise a support bearing a red-sensitive silver halide emulsion unit having associated therewith a cyan dye image-providing material, a green-sensitive silver halide emulsion unit having associated therewith a magenta dye image-providing material, and a blue-sensitive silver halide emulsion unit having associated therewith a yellow dye image-providing material, wherein at least one of the silver halide emulsion units comprises a silver halide emulsion chemically sensitized with the described gold(I) imide compound. Each silver halide emulsion unit can be comprised of one or more layers, and various units and layers can be arranged in different locations with respect to each other.

The photographic emulsion as described can contain addenda known to be useful in photographic silver halide emulsions.

In the following discussion of useful materials in the emulsions and elements of the invention, reference will be made to *Research Disclosure*, December, 1989, Item 308119, published by Kenneth Mason Publications Ltd, Dudley Annex, 12a North Street, Emsworth, Hampshire PO 10 7DQ, England, the disclosures of which are incorporated herein by reference. The publication will be hereafter identified by the term "Research Disclosure."

The silver halide emulsions can be chemically sensitized with a chemically sensitizing concentration of at least one added chemical sensitizer, that is, in addition to the gold(I) imide compound of the invention. For example, the photographic silver halide emulsion of the invention can be chemically sensitized with a gold(I) imide compound as described and at least one sulfur or selenium sensitizer. Other combinations of chemical sensitizers known in the photographic art are useful with the gold(I) imide compounds as described. An example of a useful combination of chemical sensitizers is a combination of the gold(I) imide compound as described with a sulfur chemical sensitizer comprising a thiourea compound, such as a thiourea compound described in U.S. Pat. No. 4,810,626, disclosure of which is incorporated herein by reference. Other chemical sensitizers which can be used in combination with the described gold(I) imide compound are described in Research Disclosure, paragraph III.

The photographic silver halide emulsions of the invention can be used in combination with other silver halide emulsions known in the photographic art. For example, a cubic-grain silver halide emulsion of the invention can used in combination with a tabular-grain silver halide emulsion.

Suitable vehicles for the emulsions and emulsion layers and other layers of elements of the invention can be as described in Research Disclosure, Section IX.

The photographic emulsions and elements of the invention can contain, for example, couplers and dyes (Research Disclosure, Section VII), brighteners (Research Disclosure, Section V), antifoggants and stabilizers (Research Disclosure, Section VI), antistain agents and image-dye stabilizers (Research Disclosure, Section VII), light-absorbing and -scattering materials (Research Disclosure, Section VIII), hardeners (Research Disclosure, Section X), coating aids (Research Disclosure, Section XI), plasticizers and lubricants (Research Disclosure, Section XII), antistatic agents (Research Disclosure, Section XIII), matting agents (Research Disclosure, Section XVI) and development modifiers (Research Disclosure, Section XXI).

The photographic elements can comprise a variety of supports as described in Research Disclosure, Section XVII, and the references cited therein.

Photographic elements can be exposed to actinic radiation, typically in the visible region of the spectrum, to form a latent image as described in Research Disclosure, Section XVIII, and then processed to form a visible dye image as described in Research Disclosure, Section XIX. Processing to form a visible dye image includes the step of contacting the element with a color-developing agent to reduce developable silver halide and oxidize the color-developing agent. Oxidized color-developing agent in turn reacts with the coupler to yield a dye.

Preferred color-developing agents are p-phenylenediamines. Especially preferred are 4-amino-3-methyl-N,N-diethylaniline hydrochloride, 4-amino-3-methyl-N-ethyl-N-$\beta$-(methanesulfonamido)ethylaniline sulfate hydrate, 4-amino-3-methyl-N-ethyl-N-$\beta$-hydroxyethylaniline sulfate, 4-amino-3-$\beta$-(methanesulfonamido)ethyl-N,N-diethylaniline hydrochloride and 4-amino-N-ethyl-N-(2-methoxyethyl)-m-toluidine di-p-toluene sulfonic acid.

With negative-working silver halide, the processing step described above provides a negative image. The described elements are preferably processed in the known C-41 color process as described in, for example, *British Journal of Photography Annual of* 1982, pages 209-211. To provide a positive (or reversal) image, the color-development step can be preceded by development with a nonchromogenic developing agent to develop exposed silver halide but not form dye, and then uniformly fogging the element to render unexposed silver halide developable. Alternatively, a direct-positive emulsion can be employed to obtain a positive image. Any other processes known in the photographic art, such as processes known to be useful in processing color photographic or black-and-white photographic papers, are also useful for processing exposed photographic silver halide materials as described.

Development is followed by the conventional steps of bleaching, fixing or bleach-fixing to remove silver or silver halide, washing and drying.

The following examples further illustrate the invention.

EXAMPLE 1

Silver chloride emulsions containing cubic grains measuring an average 0.33 micrometer edge length were reacted with sulfur and gold sensitizing compounds for 30 minutes at 65° C. Use of a gold(I) compound of the present invention instead of trisodium aurous dithiosulfate also allows a sulfur sensitizer other than thiosulfate to be chosen. In this example, a sulfur sensitizer having the structure S-1 is employed.

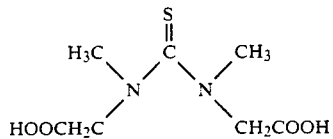

After cooling to 40° C., the emulsions were coated on film support at levels of 200 mg Ag and 600 mg gelatin per ft$^2$ with appropriate levels of surfactants, hardener and humectant added. The dried coatings were exposed sensitometrically at 365 nm for 0.1 second through a step tablet ranging in optical density from 0 to 4 units and processed for 12 minutes in developer DK-50 (trade name of and available from Eastman Kodak Company, U.S.A.). The logarithms of the relative speeds measured at 0.15 optical density unit above minimum density are shown below. The gradation of all sensitized coatings were very similar. The values of minimum density were all between 0.06 and 0.08 optical density units.

| Sensitizer | S/Au(Molar) | Log Rel. Speed |
|---|---|---|
| A None (Control) | — | 1.00 |
| B. 1.05 mg Na$_3$Au(S$_2$O$_3$)$_2$—2H$_2$O (Comparison) | 2 | 1.08 |
| C. 1.58 mg Na$_3$Au(S$_2$O$_3$)$_2$—5H$_2$O (Comparison) | 2 | 1.91 |
| D. 0.44 mg S-1, 1.04 compound 1 (Invention) | 1 | 1.97 |

The results show that the combination of a new gold(I) compound of the present invention with the sulfur sensitizer S-1 produces a small speed advantage relative to the position obtained with the optimum level of trisodium aurous dithiosulfate. More significantly, this sensitometric position is achieved using levels of both gold and sulfur sensitizers lower than the levels of trisodium aurous dithiosulfate required to reach the optimum position attainable with that reagent. Moreover, the S/Au molar ratio used in the present invention to obtain the best sensitometric position is lower than is possible to obtain with trisodium aurous dithiosulfate.

EXAMPLE 2

Silver chloride emulsions containing cubic grains measuring an average 0.40 micrometer edge length were sensitized, coated, exposed and processed as in Example 1. The results are shown below.

| Sensitizer | S/Au(Molar) | Log Rel. Speed |
|---|---|---|
| A. None (Control) | — | 1.00 |
| B. 1.05 mg Na$_3$Au(S$_2$O$_3$)$_2$—2H$_2$O (Comparison) | 2 | 1.12 |
| C. 1.58 mg Na$_3$Au(S$_2$O$_3$)$_2$—5H$_2$O (Comparison) | 2 | 1.70 |
| D. 0.664 mg S-1, 1.04 compound 1 (Invention) | 1.5 | 1.87 |

The combination of the novel gold(I) sensitizer and the sulfur sensitizer S-1 provides a significantly higher speed than trisodium aurous dithiosulfate. The speed position obtained with trisodium aurous dithiosulfate could not be increased by any further change in level of sensitizer. The superior sensitometric position of the present invention is achieved using levels of both gold and sulfur sensitizers which are lower than the levels required to reach the best position attainable with trisodium aurous dithiosulfate. Moreover, the S/Au molar ratio used in the present invention to obtain the best sensitometric position is lower than is possible to obtain with trisodium aurous dithiosulfate.

EXAMPLE 3

Silver chloride emulsions containing cubic grains with an average edge length of 0.63 micron, which were made in the presence of thioether silver halide ripeners of the type described in McBride U.S. Pat. No. 3,272,257 and containing 40 g gelatin per Ag mole were chemically and spectrally sensitized in the following manner. The chemical sensitizers listed in the Table III below were added to the emulsion samples at 40° C. Then the temperature was raised to 60° C. and held 20 minutes. 250 mg/Ag mole of a blue spectral sensitizing dye having structure S-2 was added. The emulsion samples were then doctored with 92 mg/mole Ag of the antifoggant 1-(3-acetamidophenyl)-5-mercaptotetrazole sodium salt and 218 mg KBr/mole Ag. The emulsions were coated on paper support at 26 mg Ag/ft$^2$ and 144 mg gel/ft$^2$ with 100 mg per mole Ag of a yellow color-forming coupler having the structure S-3. An overcoat containing 100 mg gel/ft$^2$ was applied with a hardener.

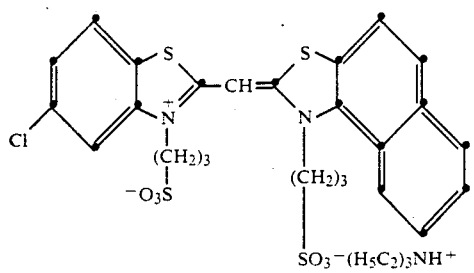

S-2

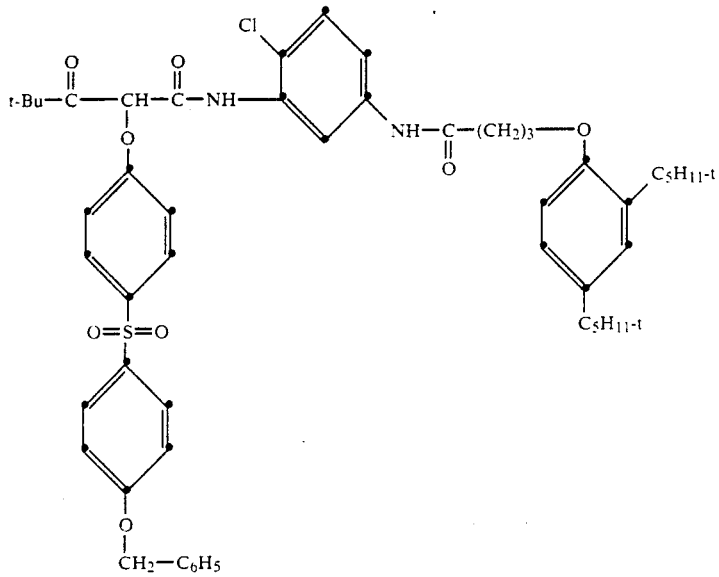

The dried coatings were exposed sensitometrically to a 3000K tungsten source for 0.1 second through a step tablet ranging in optical density from 0 to 4 units. Processing was done through a Kodak RA4 process commercially available from Eastman Kodak Co., U.S.A., (Kodak is a trademark of Eastman Kodak Com., U.S.A.). The logarithms of the relative speeds were determined at a density of 1.0 above fog. The sensitometric responses are given below.

| Sensitizer | Log Rel. Speed | Gamma |
|---|---|---|
| 0.94 mg Na$_3$Au(S$_2$O$_3$)$_2$—2H$_2$O (Comparison) | 1.00 | 190 |
| 0.44 mg Na$_2$S$_2$O$_3$—5H$_2$O, 0.93 mg compound 1 (Invention) | 1.00 | 214 |

It is seen from this data that a compound of the present invention used in combination with one molar equivalent of sulfur sensitizer results in a higher gradation (gamma) compared to sensitization with aurous dithiosulfate, which inherently contains two equivalents of the sulfur sensitizer thiosulfate.

The invention has been described in detail with particular reference to preferred embodiments thereof, but it will be understood that variations and modifications can be effected within the spirit and scope of the invention.

What is claimed is:

1. A photographic silver halide emulsion chemically sensitized with a water-soluble gold(I) compound represented by the formula:

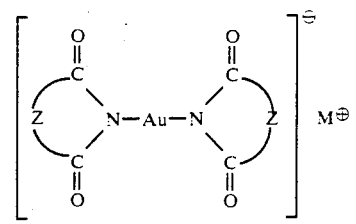

S-3 wherein:
Z represents the substituted or unsubstituted nitrogen and carbon atoms necessary to complete a 5- or 6-member imide nucleus; and
M is a cation.

2. A photographic silver halide emulsion as in claim 1 wherein Z is

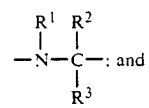

and

R$^1$, R$^2$ and R$^3$ individually are hydrogen or a hydrocarbon group of 1 to 15 carbon atoms.

3. A photographic silver halide emulsion as in claim 1 wherein Z is:

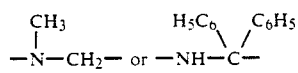

4. A photographic silver halide emulsion as in claim 1 which is a silver bromide, silver chloride, silver bromoiodide, silver bromochloride, silver chloroiodide or silver bromochloroiodide emulsion.

5. A photographic silver halide emulsion as in claim 1 also comprising a chemical sensitizing concentration of at least one added chemical sensitizer.

6. A photographic silver halide emulsion as in claim 1 also comprising a chemical sensitizing concentration of at least one added sulfur or selenium sensitizer.

7. A photographic silver halide emulsion as in claim 1 also comprising a chemical sensitizing concentration of at least one added sulfur chemical sensitizer comprising a thiourea.

8. A photographic silver halide element comprising a support bearing at least one photographic silver halide emulsion layer comprising a photographic silver halide emulsion as defined in claim 1.

9. A photographic silver halide element as in claim 8 which is a color photographic silver halide element.

10. A photographic silver halide element comprising a support bearing at least one photographic silver bromoiodide emulsion layer chemically sensitized with a gold(I) compound represented by the formula:

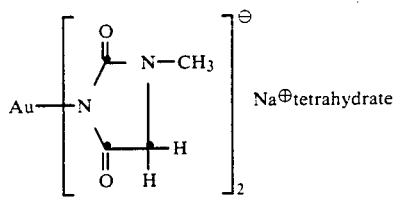

* * * * *